US00PP30132P3

(12) United States Plant Patent
Schoone

(10) Patent No.: US PP30,132 P3
(45) Date of Patent: Jan. 22, 2019

(54) ***PHALAENOPSIS* ORCHID PLANT NAMED 'DAY TRIPPER'**

(50) Latin Name: *Phalaenopsis hybrida*
Varietal Denomination: Day Tripper

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 0 days.

(21) Appl. No.: 15/731,127

(22) Filed: Apr. 25, 2017

(65) Prior Publication Data

US 2017/0311515 P1 Oct. 26, 2017

Related U.S. Application Data

(60) Provisional application No. 62/327,686, filed on Apr. 26, 2016.

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Day Tripper' particularly characterized by flowers which are purple/violet with white and a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Day Tripper'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Day Tripper'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Day Tripper' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Day Tripper' originated from a cross made by the inventor in 2003 in Strengweg, Heemskerk, The Netherlands. The female or seed parent is the *Phalaenopsis* cultivar designated 'Tinny Mist', unpatented. The male or pollen parent is the *Phalaenopsis* cultivar designated 'Tinny Honey', unpatented. The new *Phalaenopsis* 'Day Tripper' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in November, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Day Tripper', which in combination distinguish this *Phalaenopsis* as a new and distinct cultivar:

1. flowers which are purple/violet with white and a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Day Tripper', the flowers of the female parent 'Tinny Mist' are about 9 cm in size and have more white than 'Day Tripper'. The flowers of the male parent 'Tinny Honey' are about 9 cm in size and are pink with white at the edges whereas the flowers of 'Day Tripper' are 9 cm in size and purple/violet with white.

Presently, the commercial cultivar to which 'Day Tripper' can be meaningfully compared is 'Country Girl'. 'Country Girl' has less white at the edges of the flower than 'Day Tripper'. The flower and plant of 'Country Girl' are also larger in size than 'Day Tripper'.

BRIEF DESCRIPTION OF THE PHOTOGRAPHS

The accompanying photographs illustrate the overall appearance of the new *Phalaenopsis* 'Day Tripper' showing the colors as true as is reasonably possible with colored reproductions of this type. Colors in the photographs may differ slightly from the color values cited in the detailed botanical description, which accurately describe the color of 'Day Tripper'.

DETAILED BOTANICAL DESCRIPTION

Figure 1:
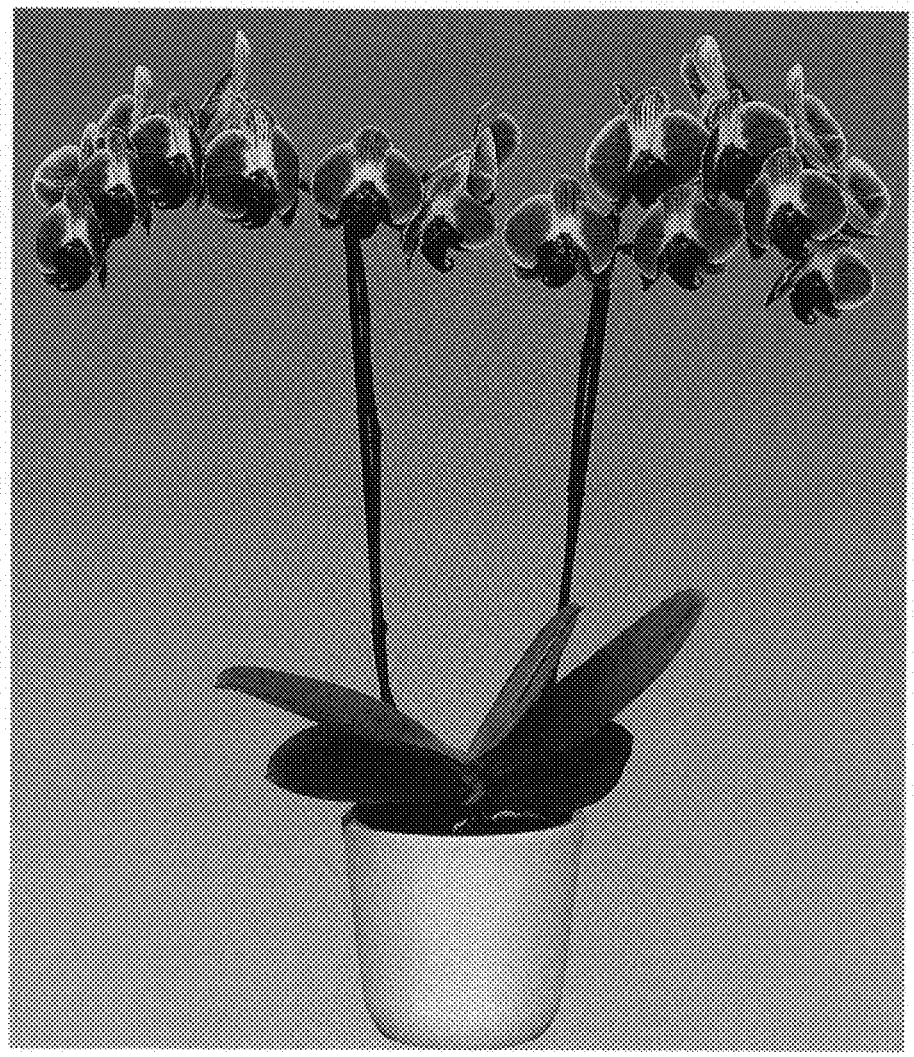
FIG. 1 shows a side view perspective of a typical flowering plant of 'Day Tripper' in a 12 cm pot, at 16 months of age.

The new *Phalaenopsis* cultivar 'Day Tripper' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Day Tripper' as grown in a greenhouse in Strengweg, Heemskerk, The Netherlands, under conditions which closely approximate those generally used in commercial practice. Initially, the ideal temperature to grow plants of 'Day Tripper' is 27° C. during the day and at night. Then, during the flowering phase of 'Day Tripper', the ideal growing temperature is 20-22° C. during the day and 18° C. at night. Light levels for growing 'Day Tripper' are a minimum of 5,000 lux and a maximum of 10,000 lux. A balanced fertilizer with level of 200 ppm N, 87 ppm P, 168 ppm K is applied. Duration of growth of 'Day Tripper' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Day Tripper' plants described is 12 months after potting.

Classification:

*Botanical.*—*Phalaenopsis hybrida.*

Parentage:

*Female or seed parent.*—*Phalaenopsis* cultivar designated 'Tinny Mist', unpatented.

*Male or pollen parent.*—*Phalaenopsis* cultivar designated 'Tinny Honey', unpatented.

Propagation:

*Type.*—Tissue culture.

*Rooting habit and description.*—Fleshy; approximately 3 mm-6 mm wide and greyed/green in color (RHS 190A); freely branching. It takes 12 weeks for plants growing in tissue culture to initiate roots.

Plant:

*Size at maturity.*—Height (from bottom of pot to highest flower): about 60 cm. Spread: about 55 cm.

*Growth habit.*—Standard; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 6-8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None.

*Mature leaf length.*—About 20 cm.

*Mature leaf width.*—About 6 cm.

*Mature leaf thickness.*—About 2 mm.

*Mature leaf color.*—Upper side: green (RHS N137A). Under side: green (RHS 137C).

*Leaf base.*—Acute.

*Margin.*—Entire.

*Venation.*—Pattern: parallel. Color of midvein: Upper side: green (RHS N137A). Under side: yellow/green (RHS 146B).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 2.

*Number of flowers per raceme.*—About 8-14.

*Length.*—About 15 cm.

*Diameter.*—About 40 cm.

Peduncle:

*Length.*—About 15 cm.

*Diameter.*—About 4 mm.

*Strength.*—Strong.

*Aspect.*—Upright.

*Texture.*—Glabrous and smooth.

*Color.*—Green (RHS 137B).

*Buds.*—Height (from base to tip): about 25 mm. Diameter (at midpoint): about 25 mm. Shape: asymmetric oval. Color: Green/white (RHS 157C) with yellow/green (RHS 145B) and some red/purple (RHS 70A). Orientation: same as flowers (forward facing).

*Flowering time.*—For an untreated plant (flowering plant that has not undergone cold-treatment where the plant grows at a temperature of 18° C. to 19° C.

for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
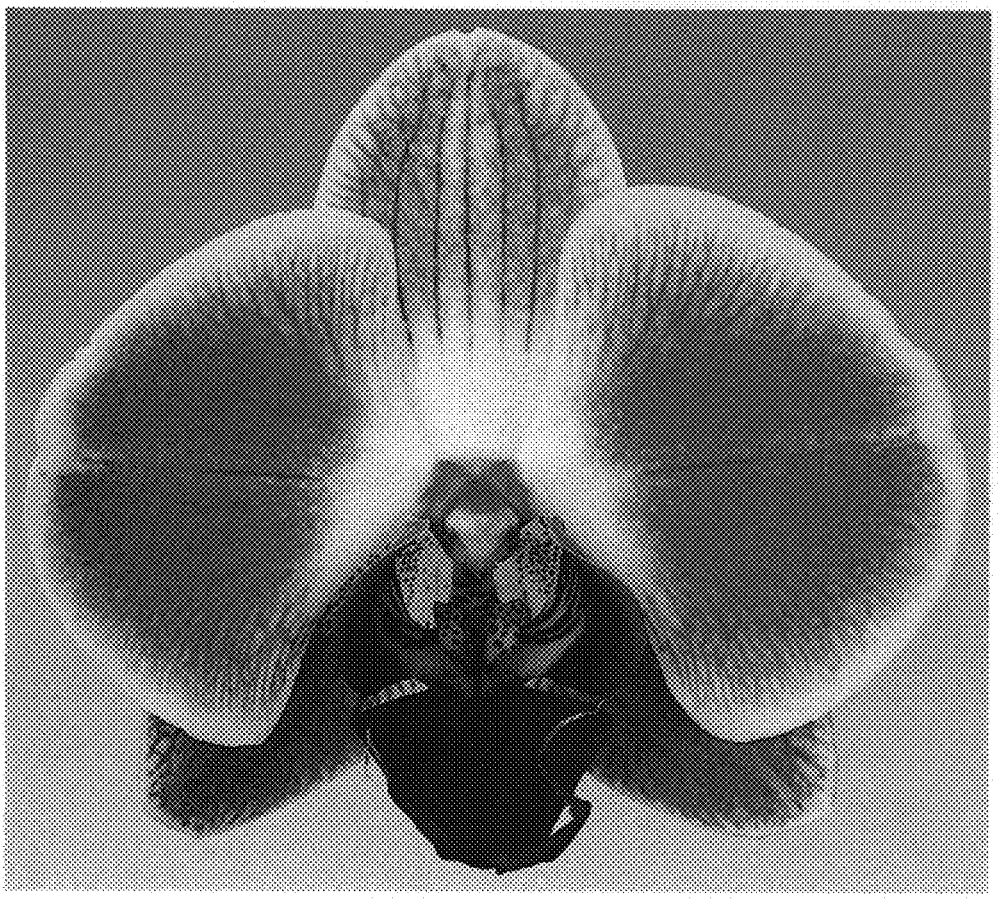
FIG. 2 shows a close-up view of the typical flower of 'Day Tripper'.
Figure 3:
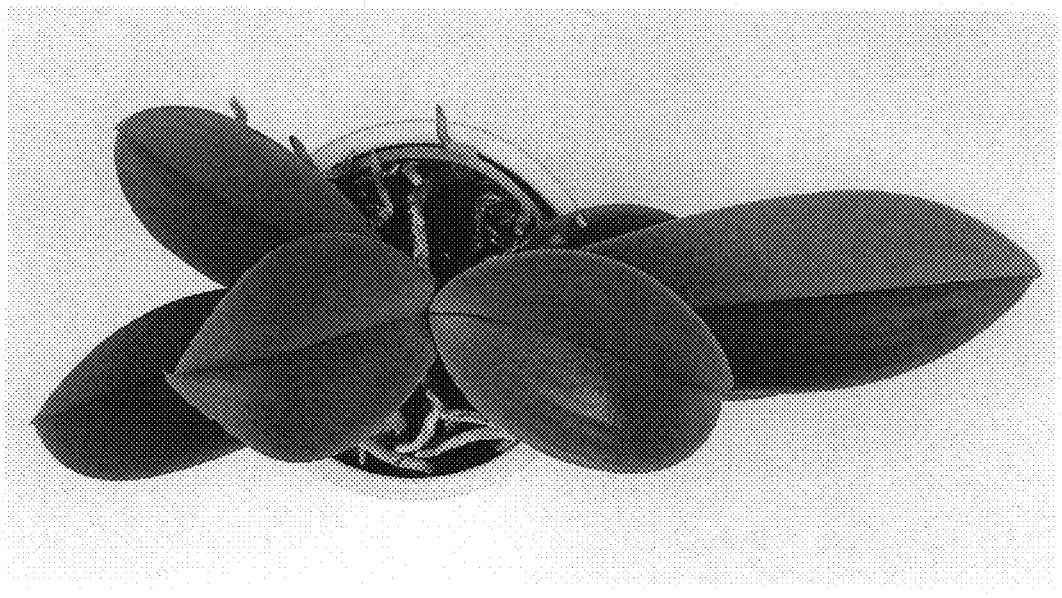
FIG. 3 shows a close-up view of the typical leaves of 'Day Tripper'.

*Flower*.—Rate of opening: Flowers fully opened about 2 to 3 days after petal and sepal separation. Orientation at opening: slanted upward and outward. Shape: Typical shape of Phalaenopsis; see FIG. 2. Size (of single bloom): Height: about 7 cm. Diameter: about 90 mm. Quantity and arrangement: three petals and three sepals. Arrangement of petals are free, not touching. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: emarginate. Margin: entire and weakly undulate. Base: broadly ovate. Length: about 55 mm. Width: about 45 mm. Texture: Upper surface: smooth and satiny. Under surface: smooth and satiny. Color (when fully opened): upper side: Main color is purple/violet, with darker purple/violet veins (RHS N81A) and in between the veins RHS N81B. Near the edges purple/violet veins with white in between (RHS NN155D). At the base and on the edges white (RHS NN155D). Under side: Main color is purple/violet (RHS N81B) with purple/violet veins (RHS N81A). At the base and on the edges white (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin of the midlobe and lateral lobes: entire and weakly undulate. Apex of the midlobe and lateral lobes: rounded. Length midlobe: about 23 mm. Width midlobe (not flattened): about 20 mm. Length lateral lobe: about 18 mm. Width lateral lobe (not flattened): about 15 mm. Depth of tube created by lateral lobes of labellum: about 15 mm. Texture of the midlobe and lateral lobes: Upper & under surface: smooth and satiny. Color (when fully opened): Mid lobe, upper side: Main color is purple (RHS N79A) with a purple/violet haze (RHS N80A). At the base and at the upper edges some yellow (RHS 12A). Under side: Main color is purple/violet (RHS N80A). In the center, from top to bottom, white (RHS NN155D). In the corners some purple (RHS N79B). Lateral lobes, upper side: Main color is purple/Violet (RHS N82A) with purple (RHS N79A) at the lower edge. At the base some white (RHS NN155D with yellow (RHS 10A) and moderate amount of purple stripes (RHS N79A). Under side: Main color is purple/violet (RHS N82A) with some purple (RHS 76C). The upper edge at the base is white (RHS NN155B). Under edge is purple (RHS N79B). Cirrhi: about 15 mm. color: purple (RHS 79A) with at the tip white (RHS NN155D). Pestle (Callosities): Length: about 4 mm. Width (not flattened): about 7 mm. Color: main color is yellow (RHS 11A) with purple spots/stripes (RHS 79B).

*Sepals*.—Arrangement: Outer whorl comprises 3 sepals, one dorsal and two lateral sepals. Overall shape: elliptical and weakly cupped. Margin: entire and weakly undulate. Length: about 45 mm. Width: about 30 mm. Apex: lateral sepal a little pointy and dorsal has a little notch. Texture: Upper and under surface: smooth and satiny. Color (when fully opened): Upper side, dorsal: purple/violet (RHS N81B) with purple/violet veins (RHS N81A) and white (RHS NN155D). Lateral: Purple/violet (RHS N81A with RHS N81B) with purple/violet veins (RHS N81A) throughout the sepal. At the base and the edges white (RHS NN155D) with at the base some yellow/green (RHS 145C). At the base a few purple/violet spots (RHS N82A). Under side, dorsal: Main color is white (RHS NN155D) with a yellow/green haze (RHS 145D). At the upper edges some purple/violet (RHS N81D) with purple/violet veins (RHS N81A). Lateral: Main color is purple/violet (RHS N81D) with purple/violet veins (RHS N81A). At the base some yellow/green (RHS 145C) and some white (RHS NN155B).

*Pedicel*.—Length: about 30 mm. Diameter: about 3 mm. Texture: glabrous and smooth. Color: starting at the flower yellow/green (RHS 145D) which runs into yellow/green (RHS 145A) with a red/purple haze (RHS 70A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 5 mm. Color: purple/violet (RHS N81A).

*Pollinia*.—Quantity: two. Diameter: about 2 mm. Color: orange (RHS 26A).

*Ovary*.—Length: about 4 mm. Diameter: about 5 mm. Color: white (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Day Tripper', as illustrated and described herein.

* * * * *